(12) United States Patent
Fish (10) Patent No.: US 10,514,337 B2
(45) Date of Patent: Dec. 24, 2019

(54) DEVICE FOR TIME CONTROLLED FLUORESCENCE DETECTION (75) Inventor: David Andrew Fish, Haywards Heath (GB)

(73) Assignee: Koninklijke Philips N.V., Eindhoven (NL)

(*) Notice: Subject to any disclaimer, the term of this patent is extended or adjusted under 35 U.S.C. 154(b) by 751 days.

(21) Appl. No.: 13/264,210

(22) PCT Filed: Apr. 6, 2010

(86) PCT No.: PCT/IB2010/051485
§ 371 (c)(1),
(2), (4) Date: Jan. 3, 2012

(87) PCT Pub. No.: WO2010/119371
PCT Pub. Date: Oct. 21, 2010

(65) Prior Publication Data
US 2012/0114528 A1 May 10, 2012

(30) Foreign Application Priority Data
Apr. 15, 2009 (EP) .................................. 09157917

(51) Int. Cl.
*G01N 21/64* (2006.01)
*C12M 1/34* (2006.01)

(52) U.S. Cl.
CPC ..... *G01N 21/6408* (2013.01); *G01N 21/6428* (2013.01); *G01N 2021/6419* (2013.01); *G01N 2021/6421* (2013.01)

(58) Field of Classification Search
None
See application file for complete search history.

(56) References Cited

U.S. PATENT DOCUMENTS

| 5,784,157 | A | 7/1998 | Gorfinkel et al. |
| 6,038,023 | A | 3/2000 | Carlson et al. |
| 2005/0051744 | A1 | 3/2005 | Emoto |
| 2006/0139634 | A1 | 6/2006 | Scott et al. |
| 2006/0239173 | A1 | 10/2006 | Zhang et al. |
| 2007/0134128 | A1 | 6/2007 | Korlach |
| 2007/0188750 | A1 | 8/2007 | Lundquist et al. |
| 2008/0037008 | A1 | 2/2008 | Shepard et al. |
| 2008/0225140 | A1 | 9/2008 | Raynor et al. |
| 2012/0114528 | A1 | 5/2012 | Fish |

FOREIGN PATENT DOCUMENTS

| EP | 1132724 A2 | 9/2001 |
| EP | 2037255 A1 | 3/2009 |
| WO | 0223166 A1 | 3/2002 |

OTHER PUBLICATIONS

By E. K. Lewis et al., "Color-Blind Fluorescence Detection for Four-Color NDN Sequencing", Proceedings of the National Academy of Sciences of the United States of America, Published online before print Mar. 30, 2005, doi: 10.1073/pnas.0501606102 PNAS, Apr. 12, 2005, vol. 102 No. 15 pp. 5346-5351.
By Zappa et al., "Photon-Counting Chip for Avalanche Detectors", IEEE Photonics Technology Letter, 17(1), 2005.
Zhu, L., et al., "Fluorescence Multiplexing with Time-Resolved and Spectral Discrimination Using a Near-IR Detector", Analytical Chemistry, May 15, 2003 American Chemical Society, U.S., vol. 75, Nr: 10, pp. 2280-2291.

*Primary Examiner* — Neil N Turk (57) ABSTRACT

The present invention provides a device for DNA sequencing, comprising DNA base calling at an early stage in the detection and processing of time controlled fluorescence detection for DNA sequencing applications.

14 Claims, 4 Drawing Sheets

DEVICE FOR TIME CONTROLLED FLUORESCENCE DETECTION

FIELD OF THE INVENTION

The invention relates to the field of DNA sequencing, especially to DNA sequencing using time controlled fluorescence detection for identification of DNA bases.

Specifically, the invention relates to a device for time controlled fluorescence detection, for DNA sequencing applications, comprising:

- A containment area for holding sequencing reaction components
- A first light source capable of emitting a first light pulse at a first wavelength, and a second light source capable of emitting a second light pulse at a second wavelength, the first wavelength being different from the second wavelength, and the first and second light pulses being incident alternately upon the containment area
- A detector pixel, arranged to cooperate with the containment area for detection of light emanating from the containment area, comprising:
  - A detector
  - An output arranged for transfer of an electrical signal from the detector pixel
- A gating means to gate the detector arranged so as not to detect the first and second light pulses emitted by the first and second light sources.

BACKGROUND OF THE INVENTION

DNA (deoxyribonucleic acid) sequencing has been known for many years. The basic concept of identifying the building blocks of the nucleic acid, containing genetic instructions used in the development and functioning of all known living organisms, has been extended from the discovery of codes to the desire to use genetic information to tackle disease.

The main role of DNA molecules is the long term storage of information. Among other functions, it contains instructions needed for construction of components of cells, in segments referred to as genes. Chemically, DNA consists of two long polymers of simple units called nucleotides, the two strands running in opposite directions to each other. Backbones between the two strands are made of sugars and phosphate groups joined by esther bonds. Attached to each sugar is one of four types of molecules called bases, of type A, C, G or T. It is the sequence of these four bases along the backbone which encodes information. By identification of these bases and their sequence, much information can be derived.

The Sanger method has been, for many years, the standard DNA sequencing technique. This method is very expensive and time consuming. Further techniques have been developed in an effort to make sequencing more efficient and affordable.

Many of the new techniques rely on fluorescent imaging for identification of the bases, known as base calling. A fluorescent moiety is attached to one particular kind of base. The fluorescence in the nucleotide is effected by absorption of light at known wavelength. The fluorescence occurs at another, slightly different, known wavelength. Detection of the fluoresced light indicates the presence of a particular base. Single color fluorescent systems exist wherein different fluids comprising sequencing reagents are washed over a sample in succession and fluorescence indicates the presence of different DNA bases in the DNA sample. Another fluorescent imaging technique is known as four color fluorescence as four different wavelengths of light are used, thereby permitting four types of nucleotide (needed for sequencing reactions) to be present in the sequencing device at the same time. Thus fluid exchanges in the device (which are very slow) can be reduced or kept to a minimum.

A type of four color fluorescent imaging is described in U.S. patent application US 2006/0139634. Other work by Lewis et al (PNAS, 2005, Vol 102, No 15, p 5346) details a temporal color flashing technique which uses continuous wave lasers, blocking filters and complex alignment optics to achieve detection of a given DNA base. Further effort has concentrated on fluorescent decay time constant discrimination, such as Zhu et al (Anal. Chem., 2003, Vol 75, No 10, p 2280). Further progress in gene sequencing is desired as the sequencing of a whole genome or re-sequencing for diseases such as cancer would have huge medical benefits.

A problem with the devices and methods described above is the slow throughput time for obtaining the sequencing information.

SUMMARY OF THE INVENTION

It is an object of the invention to improve the speed with which sequencing results are obtained.

This object is achieved according to the invention by provision of a device for time controlled fluorescence detection, for DNA sequencing applications, comprising a detector pixel which further comprises

- a first accumulator and a second accumulator, arranged to cooperate with the detector and the output,
  - The first accumulator dedicated for collection of electrical signal from the detector in response to the first light pulse incident upon the sequencing reaction components
  - The second accumulator dedicated for collection of electrical signal from the detector in response to the second light pulse incident upon the sequencing reaction components.

The sequencing reaction components comprise a sample of DNA to be sequenced and a first and a second fluorescently labeled nucleotide which are associated with specific first and second bases of the DNA sample, respectively. The first light pulse from the light source is arranged to correspond to strong absorption of the first fluorescently labeled nucleotide, such that the molecule absorbs light energy which can then be released as a fluorescent light at a different wavelength. The second light pulse is arranged to cooperate with the second fluorescently labeled nucleotide in the same way, the second fluorescence being at a different wavelength than the first fluorescence. Thus detection of fluorescent light resulting from the first or second light pulses indicates the presence of the first or second base. The detector passes on its detection information to an accumulator.

In a further embodiment of the invention, the output is arranged to provide the status of the first and second accumulators.

By associating a specific accumulator with fluorescent emission following the arrival at the sequencing reaction components of a specific light pulse, the accumulator becomes a means to directly call the DNA base detected. An accumulation of electronic signals, greater than an expected background noise or greater than a set threshold level, in an accumulator is an indication of a fluorescent response to a specific base. Thus in terms of the presence of the base, the accumulator provides a status of yes/no or 1/0. This status can then become the output from the pixel without need for provision of further electronic processing or slow transfer of analogue signal information.

In a further embodiment of the invention, a content of the first and second accumulators, is arranged for periodic transfer via the output to a processing device.

Information in the accumulators may be read out as part of an information transfer to external circuitry or device. As the base call is already facilitated by the use of the accumulators, the speed with which this information is available is greatly improved on prior art methods of sequencing.

In a further embodiment of the invention, the device further comprises a third light source capable of emitting a third light pulse at a third wavelength, and a fourth light source capable of emitting a fourth light pulse at a fourth wavelength, the third wavelength being different from the fourth wavelength, and the third and fourth light pulses being incident, sequentially, with each other and with the first and second light pulses, upon the containment area.

In a further embodiment of the invention, the detector pixel further comprises
  a third accumulator, dedicated for collection of electrical signal from the detector in response to the third light pulse incident upon the sequencing reaction components and
  a fourth accumulator, dedicated for collection of electrical signal from the detector in response to the fourth light pulse incident upon the sequencing reaction components.

These embodiments illustrate the optimum situation when all four DNA bases are to be studied simultaneously and a light source and accumulator are dedicated to each base.

In a further embodiment of the invention, the first, second, third or fourth light sources comprise a pulsed laser.

A pulsed laser, or a pulsed laser diode, is a light source that has a narrow spectral line width in comparison to other light sources. Such narrow line widths avoid issues of cross-contamination of spectral emissions, which can occur when using other light sources due to spectral overlap of the different light pulses.

In a further embodiment of the invention, the pulsed laser is fired with a period in a range between 10 ns and 1 µs, most preferably being fired with a period in a range between 100 ns and 400 ns.

In a further embodiment of the invention, the time differential between sequential firings of a first and a second pulsed laser is in a range between 10 ns and 1 µs, most preferably being 100 ns.

The periods of firing a single laser or two lasers sequentially is a trade-off between the desire for speed in the sequencing process and the ability of the detector to give a clear signal, with a good signal to noise characteristic, which can be converted into a reliable base call. The laser repetition rate should be as short as possible to excite as many fluorescent photons as possible, but in the SPAD device noise is caused by an effect known as after-pulsing, which diminishes over time (i.e. the longer the pause, the less noise affects the signal). The noise level is determined by the quality of the silicon of the detector, but generally 100 ns between pulses is efficient.

The laser repetition rate can be determined by considering the differential repetition rate times the number of lasers.

In a further embodiment of the invention, detector comprises a SPAD array.

A SPAD array is sensitive to single photon emissions, has a low noise characteristic and may be used in conjunction with CMOS transistor circuits to process the signal from the SPAD, thereby converting a single photon to a digital bit. This gives a SPAD detector advantages over slower and noisier detectors such as CCD or (independent) CMOS.

In a further embodiment of the invention, the detector pixel further comprises at least one lookup table, arranged as memory on the detector pixel.

A lookup table may be used to correct the accumulator values for biases which may occur due to, for example, quantum efficiency differences in the detector between color or wavelength of the detected light. The lookup table information should preferably be implemented before the base call is made to ensure accuracy of base call results.

In a further embodiment of the invention, the device according to the invention is included an array comprising a number of such devices.

In this manner, detector pixels paired with containment areas for holding sequencing reaction components are placed into an array. The array may, for example, be one or two dimensional. Such an array then provides for individual detection of sequencing reactions and bases comparable with a high density or moderate density sequencing. An example of high density sequencing is SOLID sequencing, wherein random arrays with millions of samples are used. Medium density sequencing is typified by the Roche/454 Life Sciences approach which utilizes around 1.6 million wells for samples.

In a further embodiment of the invention, the device according to the invention is included in an array comprising a number of devices, at least one lookup table being provided on the array.

A lookup table may be used to correct the accumulator values for biases which may occur due to, for example, quantum efficiency differences in the detector between color or wavelength of the detected light. The lookup table information should preferably be implemented before the base call is made to ensure accuracy of base call results.

BRIEF DESCRIPTION OF THE FIGURES

The invention will now be further described with reference to the figures.

DETAILED DESCRIPTION

Sequencing in the context of the present invention and its embodiments is not limited to DNA but also relates to sequencing where the end goal to detect the base pairs of a nucleic acid, for example RNA, PNA, LNA.

Figure 1:
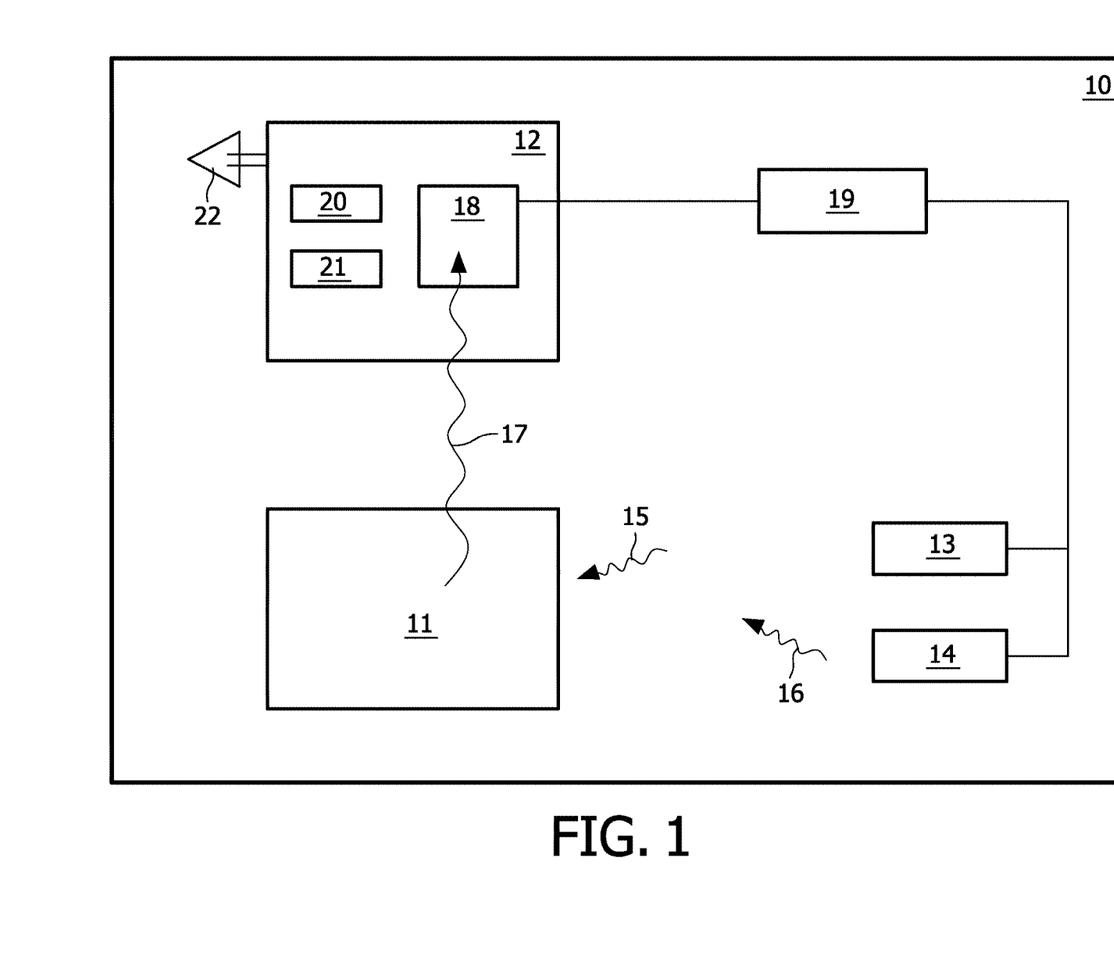
FIG. 1: schematic depiction of the device according to the invention

FIG. 1 depicts a device 10 for time controlled fluorescence detection for DNA sequencing applications according to the invention. A containment area 11 is provided where samples of DNA to be sequenced, fluorescently labeled nucleotides, and other components required for sequencing reactions (not shown) may be located. The containment area 11 can comprise, for example, a flat surface or a hollow in a substrate or a well. This containment area 11 is paired with a detector pixel 12. Here the term "pixel" is defined as a device region dedicated to the detection and processing of light emanating from the containment area 11. The device is provided with a first light source 13 and a second light source 14, which emit a first light pulse 15 at a first wavelength and a second light pulse 16 at a second wavelength, respectively. The first wavelength is different from the second wavelength and both are chosen for optimal interaction with particular fluorophores associated with particular DNA bases, A, C, G, or T, in the sample of DNA to be sequenced.

The first light pulse 15 is incident on the sequencing reaction components (not shown). Absorption of light from the first light pulse 15 by a fluorescently labeled nucleotide (not shown), results in the emission of fluorescence, the fluorescent light 17 being detectable by a detector 18 located in or on the detector pixel 12. The fluorescent light 17 is indicative of the presence of a specific DNA base. The second light pulse 16, incident on the sequencing reaction components sequential or alternate to the first light pulse, interacts with a different fluorescent nucleotide in a similar manner to indicate the presence of another specific DNA base. The device is provided with a gating means 19, which prevents direct detection of the first 15 and second 16 light pulses by the detector 18, so only fluorescent light 17 is detected. Effectively this means that there is a detection period after the emission of the first light pulse 15, the detector is then rendered inactive via the gating means 19 during the firing of the second light pulse 16 and its arrival at the sequencing reaction components, the detector is activated for a detection period after the emission of the second light pulse 16, and again rendered inactive by action of the gating means 19 before the generation of another light pulse by the first light source 13. This cycle continues with alternate firings of the first 13 and second 14 light sources.

The detector pixel 12 further comprises a first accumulator 20 and second accumulator 21. The first accumulator 20 is dedicated to collect detection information from the detector 18 during the detection interval following the arrival of the first light pulse 15 at the sequencing reaction components. In this way, the first accumulator 20 is effectively dedicated to the detection of a specific DNA base. The second accumulator 21 is dedicated to collect detection information from the detector 18 during the detection interval following the arrival of the second light pulse 16 at the sequencing reaction components. In this way, the second accumulator 21 is similarly dedicated to the detection of a (different) specific DNA base. Information from the accumulators on base detection is accessed via an output 22 from the detector pixel.

Figure 2:
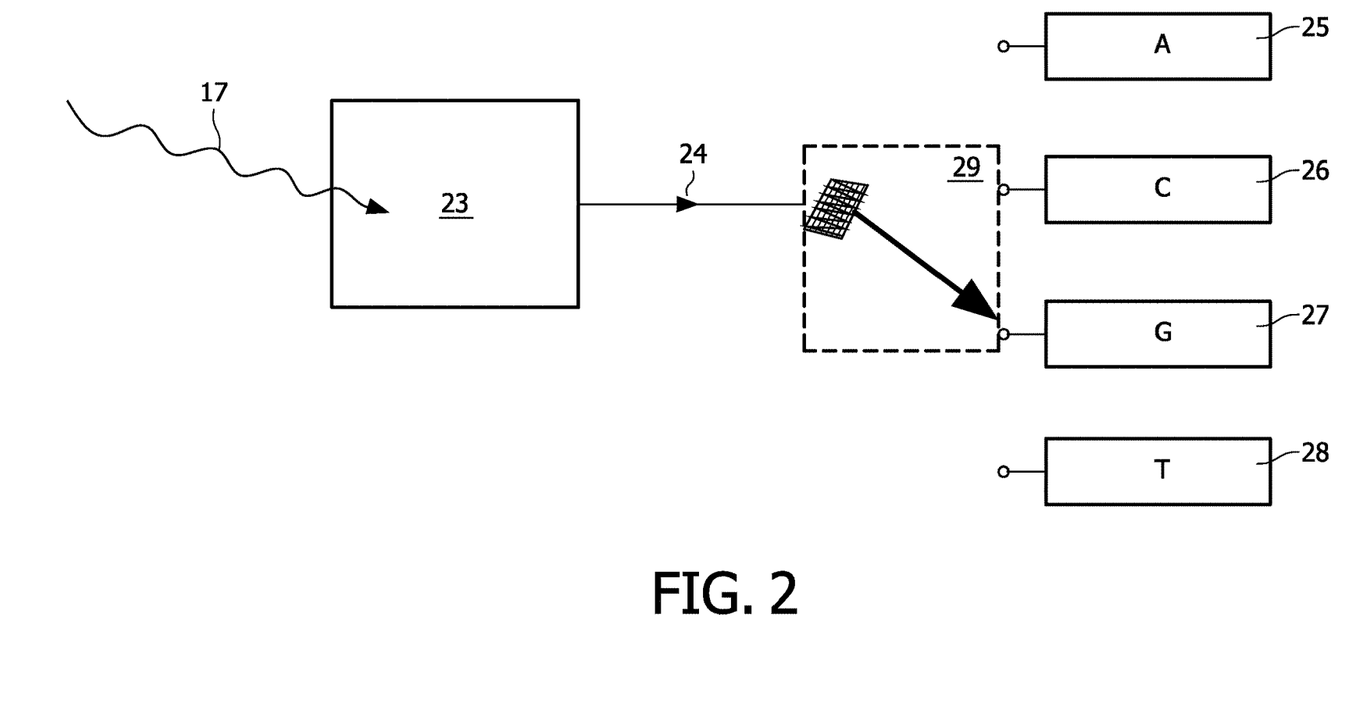
FIG. 2: shows a section of an embodiment of the invention comprising SPAD detector and four accumulators

FIG. 2 schematically illustrates a section of an embodiment of the current invention where the detector 18 is a SPAD (single photon avalanche photodiode) detector 23 arranged to detect fluorescent light 17 emitted from sequencing reaction components (not shown). The embodiment comprises four pulsed light sources (not shown), the device being arranged to detect four DNA bases A, C, G and T, and being operated as described above. The embodiment further comprises four accumulators 25, 26, 27 and 28, dedicated to bases A, C, G and T, respectively, which are fed signal information 24 relating to detected fluorescence from the SPAD detector 23, according to which of the four light pulses has been fired. A switch 29 directs the SPAD detector information to the correct accumulator 25, 26, 27 or 28, the signal information from the SPAD detector 23 being available to only one accumulator at a time. A thresholding means (not shown) may be added to assess the accumulator contents, or compare against desired signal levels, to improve data reliability for DNA base calling.

The embodiment is described in terms of accumulators, but in order to simplify pixel design, it is also possible to use a 1 bit memory as an alternative to an accumulator.

The embodiment is described in terms of SPAD detectors, but other detectors, especially single photon detectors, may be used. However, the SPAD has considerable advantages.

In a scheme as suggested in FIG. 2, the detector is disabled when the pulsed light source, e.g. a pulsed laser is on and enabled when it is off. For a case where four light colors are fired at 10 ns intervals, certainty from one 10 ns detection time would not be assured, but 1000 such events could determine a base to very high accuracy. Overall, for this example, 40 µs would be needed. This is orders of magnitude faster than any prior art sequencing scheme can operate.

The SPAD has sub-nanosecond response speeds and can be actively reset within a nanosecond using CMOS circuitry that occupies the same silicon substrate as the SPAD detector. The single photon nature of the SPAD detector will mean that a significant number of detection windows will not detect a photon because of, for example, direction of emission of the photon away from the detector, imperfect quantum efficiency of the detector, or noise causing the detector to fire. Perhaps only 10% of photons are detected. However, even in a (lower limit) 40 ns period, around 100 photons would be detected. Thermal noise for a 2 µm by 2 µm SPAD device at room temperature is around 5 counts/sec and therefore almost negligible within 40 µs. Assuming 80% of photons originate from the correct fluorescence for a particular base. (Although this may vary—some prior art instruments achieve only 40 to 60% due to crosstalk arising from overlapping spectra). Assume a maximum rate of bases incorporated into a DNA strand for sequencing to be around 1 kHz. Several orders of magnitude of detection windows are possible e.g. ×250, giving 25000 photons, cutting counting errors from around 10% to 0.6%, and thereby enabling high confidence even in the presence of significant cross talk.

Figure 3:
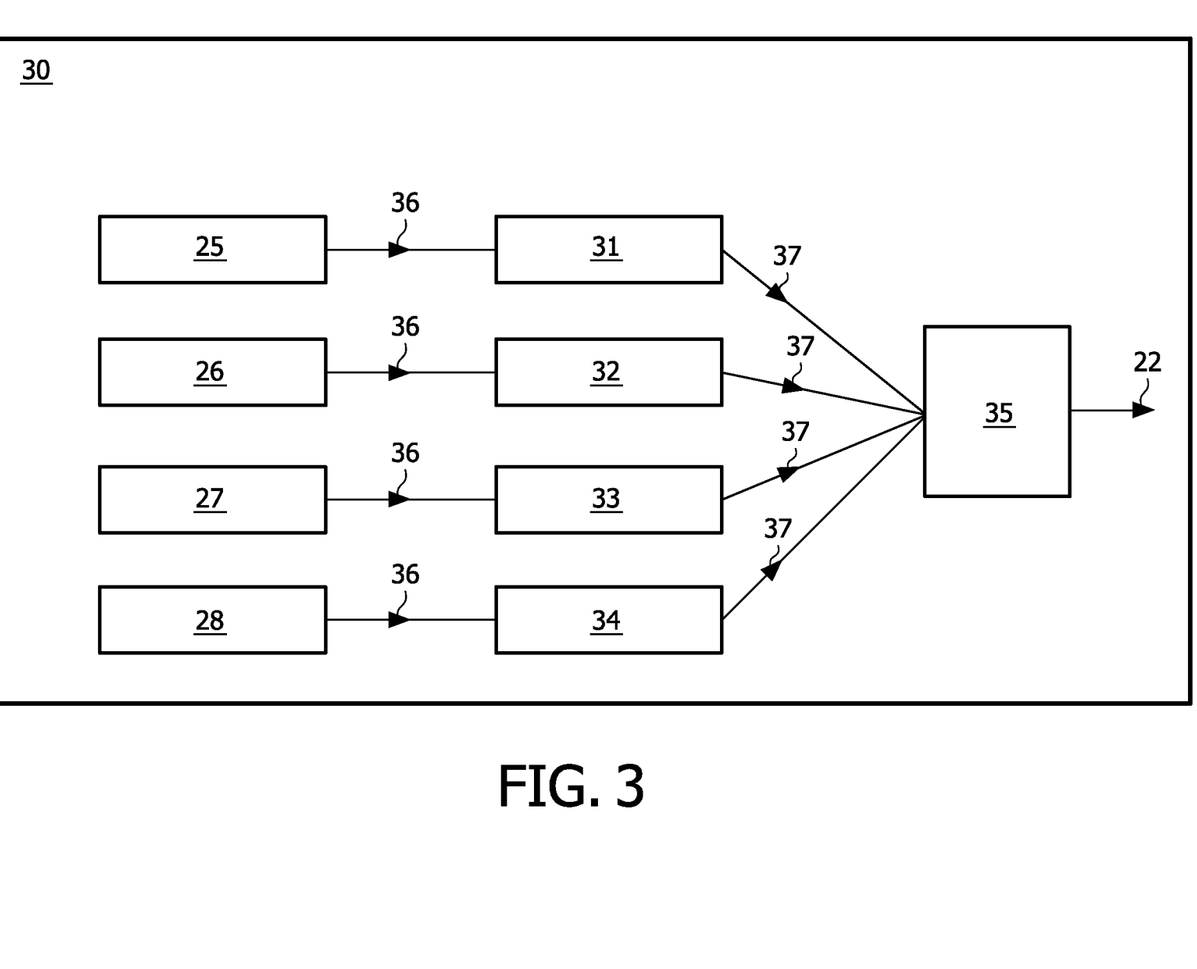
FIG. 3: shows a section of an embodiment of the invention comprising lookup tables

FIG. 3 illustrates a part of an embodiment of the invention 30 comprising lookup tables. Accumulator values are passed to a lookup table before base call, indicated by arrows 36. In the embodiment shown, four lookup tables 31, 32, 33, and 34 are provided but it may not always be necessary to provide four. In some cases, only one may be needed, for example, either individually for a single accumulator or one to serve all accumulators 25, 26, 27, and 28. The necessity of providing a lookup table 31, 32, 33 and 34 depends on the performance of the device in relation to the detection of the fluorescent light emitted. Detector efficiencies vary between colors or wavelengths and this may introduce a bias in the counted values. The purpose of the lookup tables 31, 32, 33 and 34 is to undo the bias before any bases are called, thereby improving the quality and reliability of the result. Data accuracy is a very important issue, particularly relevant when sequencing information is used for clinical applications. The maximum count can be transferred to (indicated by arrows 37) and used by further processing means 35 to call a base by comparison with other accumulators or by comparison with a known threshold for output 22.

As an example, the detector pixel which would implement the maximal photon count to achieve a base call may comprise of a silicon substrate capable of implementing SPAD devices (preferably sensitive from the blue through to deep red and near infrared wavelengths) with deep-submicron CMOS transistor devices. The SPAD may be buffered using an inverter, with any output being feedback to the SPAD to create an active reset, in a known manner. Switching accumulators to enable base calling at the pixel level requires synchronization to the relevant detection window, as discussed above.

The accumulators could be implemented in, for example, a digital manner using a counter and a readout latch or an analogue manner using, for example, a charge pump that cycles a small charge stored from the SPAD firing once onto a larger storage capacitor that gradually increases in voltage as multiple firings of the SPAD occur across many detection windows. The associated pixels should be as small as possible to enable the highest density of sequencing sites. Using deep sub-micron CMOS in the detection hardware, a 50 µm by 50 µm pixel is foreseen.

Figure 4:
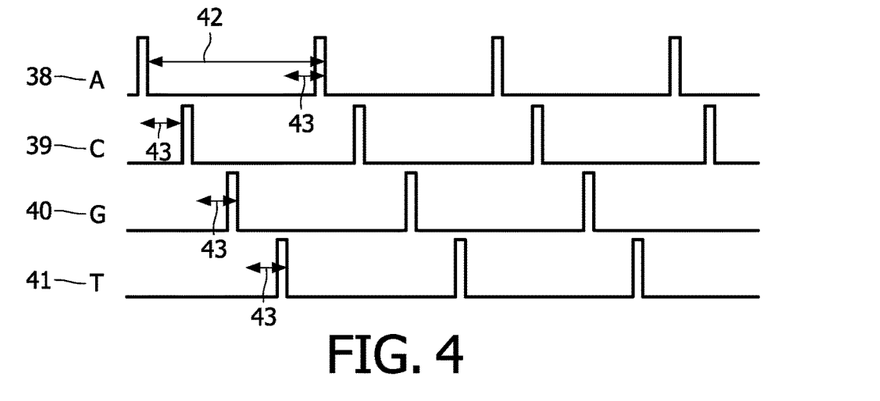
FIG. 4: illustrates the sequential firing of pulsed laser light sources according to the invention

FIG. 4 further illustrates the sequential firing of pulsed laser light sources according to the invention. This embodiment illustrates timings which are considered as a possible optimum set of timings, but should not be considered as limiting.

A pulsed light source, here illustrated in terms of a pulsed laser, is dedicated for detection of each of the four DNA bases, A, C, G, and T. The firing schedules 38, 39, 40 and 41 for each laser are shown in the figure together with the associated DNA base. Each laser (not shown) is indicated as firing with a period indicated by arrow 42. An optimal period for this time period is around 400 ns, especially between 100 ns and 400 ns, but it may be in the range between 10 ns and 1 µs. A delay period between successive firings of different lasers is shown as indicated by arrows 43, which may also be in the range between 10 ns and 1 µs, but preferably in the range between 100 ns and 400 ns. Here all the delay periods are illustrated as identical but this should not be construed as limiting. The delay period between successive firings 43, as shown here, is 100 ns in relation to a pulse period 42 of 400 ns.

As can be seen from the figure, the first laser is fired 38 and within a time period 43, the second laser is fired. Between these two firings the detector (not shown) can be set to register any fluorescent light coming from the sequencing reaction components (not shown) which will then be assigned as indicative of the presence of a DNA base A. Between the sequential firings 39, 40 of the second and third lasers, detected fluorescence will be attributed to DNA base C, and so on.

Figure 5:
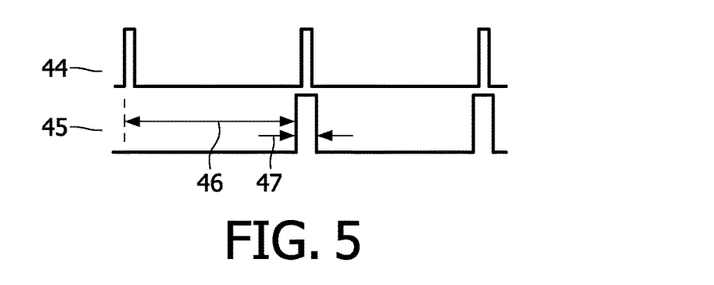
FIG. 5: illustrates gating of the detector during laser firing according to the invention

FIG. 5 illustrates gating of the detector during laser firing according to the invention. A laser firing sequence 44 is illustrated in the figure. Only one laser (not shown) is considered here for clarity but, the detector gating applies to the firing of any laser or other pulsed light source. The detector gating signal 45 is also illustrated in the figure. The detector (not shown) is gated during firings of the laser so that laser light is not detected. The detector is thereby dedicated to the receipt of fluorescent light from the sequencing reaction reagents (not shown) which is triggered by the initial laser light incident on the sample. Two delays are illustrated in the figure as indicated by arrows 46 and 47. The first delay 46 is caused by the first pulse from the laser (synchronized) and then the gating signal rises just before the next firing of the laser is due to arrive. A second delay 47 is then generated to keep the gating signal operational until the laser pulse has passed. This means that the first laser pulse is not gated and any signal detected can be ignored.

Figure 6:
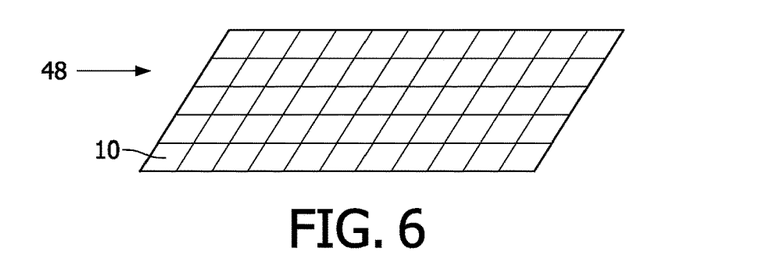
FIG. 6: illustrates an array of devices according to the invention.

FIG. 6 shows an array 48 of devices according to the invention. Is it envisaged that a series of DNA samples or fragments to be sequenced can be placed in a multiplicity of containment areas according to the invention, each containment area being paired with detectors, accumulators etc, (not shown), as described above, so that base calling for each DNA sample or fragment occurs within each detector pixel 12. In a single device 10, each pulsed light source can provide light to all the containment areas. Thus the containment areas 11, detector pixels 12 and outputs 22 are provided in multiplicity but it is not preferable that the light sources 13 or 14 or gating means 19 are also provided in multiplicity. The information can then be accessed as a result, rather than as electronic detector output yet to be processed. This reduces information transfer load and speeds up the sequencing process. It is further envisaged that output from the detector pixels 12 may be periodically collected row by row for example, to further speed up processing. Also envisaged is a single or a series of lookup tables which serve more than one or one set of accumulators. The lookup tables may be removed from the detector pixel to be located elsewhere on the array construction or external to the array. By directing the output of multiple detector pixels to a single or reduced number of lookup tables, speed is gained in the processing of the sequencing information. For example, a lookup table relevant to detection of DNA base A could be accessed by a single row of detector pixels on the array, and so on.

The array of devices facilitates sequencing as described above. As lasers and detectors can be separated by some distance, however, synchronization between the two can become difficult due to delays in electronic signals. The lasers must illuminate larger areas simultaneously. This can be further improved. As the laser pulse is sub-nanosecond, timing delays across the detector become too large to gate all pixels accurately. Thus a further embodiment of the invention comprises a synchronization effect that detects the laser pulse in every detector pixel 12, or for a small number of detector pixels defined as a group. A local signal to gate the fluorescence detecting detectors against the laser may be produced. The local signal should be generated within or close to the devices so that delays are kept to a minimum and delays are relatively constant across different regions of the array. That is to say, the distance between laser detection and fluorescence detection should be standardized so far as possible across the array 48.

Figure 7:
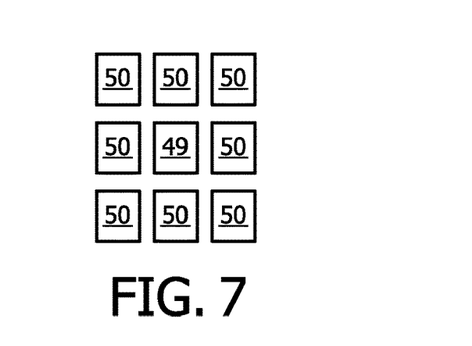
FIG. 7: show a further embodiment of the invention for an array of devices

FIG. 7 further illustrates this concept in terms of a further embodiment for an array of devices according to the invention, the preferred option being shown in the figure. Laser and fluorescence detection subpixels are defined on the array 48, the term subpixel here indicating that each paired containment area 11 and detector pixel 12 now form part of a larger group, the detector from each pair having a specified function with respect to the laser light or the fluorescent light. In FIG. 7 the central subpixel 49 is arranged to detect the laser light pulse, thereby triggering the generation of a gating clock for nearby fluorescence pixels 50. Other shapes and arrangements of laser and fluorescence subpixels are possible, and more or less fluorescence detection subpixels 50 can be linked to a laser detection pixel 49.

To facilitate this arrangement, the sequencing array must match the detector. For the embodiment shown in FIG. 7 this means that within every 3×3 sequencing sites or containment areas 11, the central site or containment area 11 should be nonfunctional and preferably scattering. The preference for a scattering site is to cause laser photons to be strongly directed towards the detector so that the laser detection subpixel detects the beginning of the laser pulse as early as possible, thereby reducing the chance of the fluorescent detection being operated. The central site or containment area 11 should preferably be non-functional, i.e. not capable of producing fluorescence. Gating of the fluorescence subpixels can be effected as described above for a single device.

The invention has been described above in terms of a single fluorescent emission originating from a single DNA base. However, this should not be construed as limiting as it is possible to arrange the sequencing process such that the fluorescent emission is indicative of two or more neighboring DNA bases in the sequence. For example, the fluorescent moiety may be linked to two coupled DNA bases located on the sequence, the sequencing reaction being designed to simultaneously determine the presence of the two coupled DNA bases. Sequencing by ligation is an example. The invention can be applied in the same manner as for single bases, being dependent on how the fluorescence is defined and utilized.

LIST OF REFERENCE NUMERALS

10 Device
11 Containment area
12 Detector pixel
13 First light source
14 Second light source
15 First light pulse
16 Second light pulse
17 Fluorescent light
18 Detector
19 Gating means
20 First accumulator
21 Second accumulator
22 Output
23 SPAD detector
24 Indication of signal information
25 Accumulator
26 Accumulator
27 Accumulator
28 Accumulator
29 Switch
30 Embodiment of the invention comprising lookup tables
31 Lookup table
32 Lookup table
33 Lookup table
34 Lookup table
35 Processing means
36 Arrow indicating transfer of information from accumulator to lookup table
37 Arrow indicating transfer of information from lookup table to processing means
38 Laser firing schedule for DNA base A
39 Laser firing schedule for DNA base C
40 Laser firing schedule for DNA base G
41 Laser firing schedule for DNA base T
42 Arrow indicating firing period for single laser
43 Arrow indicating firing period between sequentially fired lasers
44 Laser firing sequence
45 Detector gating signal
46 Delay 1
47 Delay 2
48 Array
49 Laser detection subpixel
50 Fluorescence detection subpixel

The invention claimed is:

1. A device for time controlled fluorescence detection for DNA sequencing applications comprising:
   a containment area including sequencing reaction components including fluorescent labeled nucleotides;
   a first light source configured to emit a first light pulse at a first wavelength, and a second light source configured to emit a second light pulse at a second wavelength, the first wavelength being different from the second wavelength, and the first and second light pulses being incident alternately upon the containment area;
   a detector pixel, arranged to cooperate with the containment area, the detector pixel comprising:
      a photodetector configured to detect and process light emanating from the containment area to produce detection information comprising an electrical signal; and
      an output configured to transfer the electrical signal from the detector pixel;
   a gate configured to deactivate the photodetector rendering the photodetector inactive during firings of the first light pulse and second light pulse, thereby preventing the photodetector from direct detection of the first and second light pulses emitted by the first and second light sources, wherein
   the detector pixel further comprises a first accumulator and a second accumulator, arranged to cooperate with the photodetector and the output,
   the first accumulator configured to collect the detection information from the photodetector when the first light pulse incident upon the sequencing reaction components to detect a specific DNA base that has a fluorescent label that exhibits strong absorption of the first light pulse having the first wavelength; and
   the second accumulator configured to collect the detection information from the photodetector when the second light pulse incident upon the sequencing reaction components to detect a different specific DNA base that has a fluorescent label that exhibits strong absorption of the second light pulse having the second wavelength.

2. A device as claimed in claim 1, wherein the output is configured to provide information from the first and second accumulators concerning base detection.

3. A device as claimed in claim 1, wherein the device is configured to periodically transfer the detection information collected by the first and second accumulators via the output to a processing device.

4. A device as claimed in claim 1, wherein the device further comprises a third light source configured to emit a third light pulse at a third wavelength, and a fourth light source configured to emit a fourth light pulse at a fourth wavelength, the third wavelength being different from the fourth wavelength, and the third and fourth light pulses being incident, sequentially, with each other and with the first and second light pulses, upon the containment area.

5. A device as claimed in claim 4, wherein the detector pixel further comprises:
   a third accumulator, dedicated for collection of the detection information from the photodetector when the third light pulse incident upon the sequencing reaction components; and
   a fourth accumulator, dedicated for collection of the detection information from the photodetector when the fourth light pulse incident upon the sequencing reaction components.

6. A device according to claim 4, wherein the first, second, third or fourth light sources comprise a pulsed laser.

7. A device according to claim 6, wherein the pulsed laser is pulsed with a period in a range between 10 ns and 1 μs.

8. A device according to claim 6, wherein the time differential between two sequential firings of the pulsed laser is in a range between 10 ns and 1 μs.

9. A device according to claim 1, wherein the photodetector comprises a SPAD array.

10. A device according to claim 1 wherein
the detector pixel includes memory;
at least one lookup table is stored in the memory of the detector pixel; and
the device includes a processor that is configured to analyze the detection information with respect to the lookup table.

11. An array comprising:
a plurality of containment areas including sequencing reaction components including fluorescent labeled nucleotides;
a plurality of detector pixel, paired with a containment area and arranged to cooperate with the paired containment area, each detector pixel of the plurality comprising:
   a photodetector configured to detect and process light emanating from the containment area to produce detection information comprising an electrical signal; and
   an output configured to transfer the electrical signal from the detector pixel;
one or more first light sources configured to emit a first light pulse at a first wavelength;
one or more second light source configured to emit a second light pulse at a second wavelength, the second wavelength being different from the first wavelength, and the first and second light pulses being incident alternately upon the containment area, wherein;
gate circuitry configured to deactivate the photodetector rendering the photodetector inactive during firings of the first light pulse and second light pulse, thereby preventing the photodetector from direct detection of the first and second light pulses emitted by the first and second light sources, wherein
the detector pixel further comprises a first accumulator and a second accumulator, arranged to cooperate with the photodetector and the output,
   the first accumulator configured to collect the detection information from the photodetector when the first light pulse incident upon the sequencing reaction components to detect a specific DNA base that has a fluorescent label that exhibits strong absorption of the first light pulse having the first wavelength; and
   the second accumulator configured to collect the detection information from the photodetector when the second light pulse incident upon the sequencing reaction components to detect a different specific DNA base that has a fluorescent label that exhibits strona absorption of the second light pulse having the second wavelength.

12. The array according to claim 11 wherein a memory including at least one lookup table is provided on the array, wherein the array further includes a processor that is configured to analyze the detection information with respect to the lookup table.

13. A device according to claim 6, wherein the pulsed laser is pulsed with a period in a range between 100 ns and 400 ns.

14. A device according to claim 6, wherein the time differential between two sequential firings of the pulsed laser is 100 ns.

* * * * *